(12) United States Patent
Chen et al.

(10) Patent No.: US 9,279,111 B2
(45) Date of Patent: Mar. 8, 2016

(54) LEECH HYALURONIDASE AND ITS APPLICATION

(71) Applicants: Jian Chen, Wuxi (CN); Guocheng Du, Wuxi (CN); Zhen Kang, Wuxi (CN); Peng Jin, Wuxi (CN)

(72) Inventors: Jian Chen, Wuxi (CN); Guocheng Du, Wuxi (CN); Zhen Kang, Wuxi (CN); Peng Jin, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 14/251,579

(22) Filed: Apr. 12, 2014

(65) Prior Publication Data

US 2015/0031085 A1     Jan. 29, 2015

(30) Foreign Application Priority Data

| Jul. 29, 2013 | (CN) | 2013 1 0323064 |
| Aug. 15, 2013 | (CN) | 2013 1 0358573 |
| Oct. 22, 2013 | (CN) | 2013 1 0498577 |
| Nov. 22, 2013 | (CN) | 2013 1 0597818 |
| Jan. 8, 2014 | (CN) | 2014 1 0007408 |

(51) Int. Cl.
  *C12N 9/24* (2006.01)
  *C12P 19/26* (2006.01)
  *C12P 21/02* (2006.01)

(52) U.S. Cl.
  CPC .............. *C12N 9/2402* (2013.01); *C12P 19/26* (2013.01); *C12Y 302/01036* (2013.01); *C12P 21/02* (2013.01)

(58) Field of Classification Search
None
See application file for complete search history.

(56) References Cited

U.S. PATENT DOCUMENTS 7,049,124 B1 *   5/2006   Kordowicz et al. ........... 435/201

* cited by examiner

*Primary Examiner* — Suzanne M Noakes
(74) *Attorney, Agent, or Firm* — Lili Chen (57) ABSTRACT

The present invention provides a novel leech HAase and a method of producing low-molecular-weight HA oligosaccharides using the leech HAase. This invention successfully cloned the first leech HAase gene and provides a method for high-level expression of the leech HAase gene. By controlling the incubation condition, different HA oligosaccharides, particularly HA4, HA6, HA8 and HA10, can be selectively generated using the leech HAase. The large-scale expression of the leech HAase and the enzymatic production of specific HA oligosaccharides are not only useful for the cosmetic, healthcare and the medical industries but also can be a great help to polysaccharides chemical synthesis and cancer research.

3 Claims, 9 Drawing Sheets

LEECH HYALURONIDASE AND ITS APPLICATION

CROSS-REFERENCES AND RELATED APPLICATIONS

This application claims the benefits of priority to Chinese Application No. 201410007408.1 entitled "A novel hyaluronidase and its production and purification", filed Jan. 8, 2014, which claims the benefit of priority to Chinese Application No. 201310323064.0, filed Jul. 29, 2013; and Chinese Application No. 201310597818.1, entitled "A method of effectively expressing hyaluronidase", filed Nov. 22, 2013, which claims the benefit of priority to Chinese application No. 201310358573.7, filed Aug. 15, 2013; and Chinese Application No. 201310498577.5, entitled "An enzymatic method of producing low-molecular-weight HA", filed Oct. 22, 2013, which are herein incorporated by reference in their entirety.

BACKGROUND OF THE INVENTION

1. Field of the Invention

The present invention relates to the field of enzymatic engineering, and more particularly relates to a novel leech hyaluronidase.

2. Description of the Related Art

Hyaluronic acid (HA) is a linear and unbranched high-molecular-weight polysaccharide composed of repeating disaccharide D-glucuronic acid (GluUA) and N-acetyl-D-glucosamine (GlcNAc) units linked through β-1,4 bonds. High-molecular-weight HA is widely distributed among various host tissues and participates in numerous physiological processes. The biological functions and applications of HA depend on its molecular mass. In particular, low-molecular-weight HA oligosaccharides have unique biological activities. Smaller HA oligosaccharides can stimulate fibroblast proliferation and collagen synthesis and selectively kill many types of cancer cells via disruption of the receptor-hyaluronan interaction. In addition, low-molecular-weight HA oligosaccharides are easily absorbed by the body and serve as precursors for the synthesis of both higher-molecular-weight HA molecules and other substances. Thus, a specific narrow spectrum of HA oligosaccharides could have broad applications in medicine, food and cosmetics. Low-molecular-weight HA is mainly produced by the degradation of high-molecular-weight HA by physical and chemical methods. However, the products of these methods have a broad range of molecular weight, making it difficult to obtain HA oligosaccharides with specific molecular weight. Many chemical approaches are time-consuming. Rare carbohydrate oligosaccharide backbones and expensive substrate also limited the large scale application of those chemical methods. In contrast, the enzymatic production of HA oligosaccharides with a well-characterized HAase is promising and attractive because of its unique advantages, such as mild operation conditions and high product specificity.

Hyaluronidases (HAases) which can degrade HA are found to be involved in many important biological processes, such as cell division, cell connection, activity of germ cell, DNA transfection, embryonic development, tissue repair and cell proliferation. HAases are a large family of glycosidase that are widely distributed in eukaryotes and procakyotes. According to substrate specificities and hydrolysis products, HAases are divided into three classes: hyaluronate 4-glycanohydrolases (EC 3.2.1.35, Bovine testicular hyaluronidase, BTH), hyaluronate lyases (EC 4.2.2.1, *Streptococcus* hyaluronate lyase) and hyalutonate 3-glycanohydrolases (EC 3.2.1.36, Leech HAases).

Hyaluroniases from leech is a representative enzyme of the third class of hyaluroniases. Leech HAase has higher substrate specificity and a narrow-spectrum. It degrades high-molecular-weight HA to HA tetrasaccharides (HA4) by catalyzing the hydrolysis of β-1,3-glucosidic bond. Because of its high substrate specificity, leech HAase can not degrade chondroitin or chondroitin sulfate. In addition, activity of leech HAase is unaffected by heparin. Therefore, leech HAases have great potential in clinical applications.

Currently, leech HAase is mainly obtained by extracting from living leech tissue. The limited source and tedious extraction process have impeded the application of leech HAase in medical application and scientific research.

There is a need for providing an easy source of leech HAases and an effective method of producing low-molecular-weight HA using the HAases. The present invention sacrifices this need and provides other benefits as well.

DETAILED DESCRIPTION

The goal of the present invention is to provide a novel leech HAase and a method of producing low-molecular-weight HA by use of the leech HAase.

The nucleotide sequence of the leech HAase gene (HaseA3887) is set forth in SEQ ID NO.1.

The nucleotide sequence of the HAase gene could be a sequence with one or several nucleotides substituted, or deleted or added based on SEQ ID NO.1.

The nucleotide sequence of the HAase gene could also be a sequence which has 85% similarity of SEQ ID NO.1.

The amino acid sequence of HAase is set forth in SEQ ID NO.3.

The present invention also provides 1) a nucleotide sequence encoding a polypeptide of SEQ ID NO:3; 2) a nucleotide sequence with one or several nucleotides substituted, deleted, or added based on a nucleotide sequence of 1); 3) a nucleotide sequence having 85% identity with a sequence of 1).

The present invention also provides an effective method of overexpressing HaseA3887. The expression of HaseA3887 is optimized by fusing 6 His tags to its N-terminus. Fusing 6×His tag to the N-terminus of HaseA3887 not only made the purification process easier but also significantly improved the HAase activity. The method comprises the following steps:

(1) Plasmid construction: to construct the recombinant plasmid in which 6 His tags were fused to the N-terminus of HaseA3887, the gene HaseA3887 was amplified with primers BYA3887HF/BYA3887R. The PCR products were digested with EcoRI/NotI and ligated into EcoRI/NotI-digested pPIC9K to create pPIC9K-His-HaseA3887.

(2) Recombinant strain construction: The recombinant plasmid was linearised with SalI and then transformed into *Pichia pastoris* GS115 by electroporation.

(3) Expression of the target protein: Positive *P. pastoris* GS115 recombinants carrying HaseA3887 were cultivated in YPD medium at 30° C. 2.5 mL culture was transferred into 25 mL BMGY medium and incubated in 250-mL Erlenmeyer flask rocking at 30° C. and 200 rpm. When $OD_{600}$ of the yeast culture reached 4-6, the cells were collected and transferred to BMMY induction medium and cultivated at 30° C., 200 rpm for 96 hours. The culture was fed with 1% (v/v) methanol every 24 hours The present invention also provides a method of purifying HAase from fermentation broth. The method comprises the following steps: The fermentation supernatant containing HAase was filtered through a 0.45 μm filter membrane and loaded onto a gravity-flow column packed with Ni-NTA agarose, the column was incubated at 4° C. for 2 hours. The impurities were washed with a stepwise gradient of imidazole (0, 10, 20, 30, 40, 50 mM) in a phosphate buffer. The bound N-terminal His-tagged protein was eluted from the column with a phosphate buffer containing 500 mM imidazole, and then dialyzed to remove salts and imidazole.

The present invention also provides a method of producing low-molecular-weight HA using the leech HAase. The reaction mixture which contained high-molecular-weight HA (Molecular weight $10^4$-$10^7$ kDa) and pure leech HAase (100-13000 U/mg HA) is incubated at pH4.0-8.0, 10° C.-65° C. for 4-8 hours. Before the reaction, the high-molecular-weight HA is prepared to have a concentration of 1-100 g/L in 50 mM citrate buffer (pH5.5). The leech HAase is dissolved in water to make a enzyme solution. The reaction mixture is preferred to be incubated at pH5.5, 38° C. for 4-8 hours.

To produce decasaccharide (HA10) and octasaccharide (HA8), 0.8 mL high-molecular-weight HA (2 g/L), 8 μl HAase ($2.43 \times 10^5$ U/mL) and appropriate amount of citrate buffer (pH5.5) are mixed to form 1 mL reaction system. The mixture is incubated at 38° C. for 4 hours to generate HA10 and HA8.

To produce tetrasaccharide (HA4) and hexasaccharide (HA6), 0.8 mL high-molecular-weight HA (2 g/L), 41 μl HAase ($2.43 \times 10^5$ U/mL) and appropriate amount of citrate buffer (pH5.5) are mixed to form 1 mL reaction system. The mixture is incubated at 38° C. for 8 hours to generate HA4 and HA6.

To produce tetrasaccharide (HA4), hexasaccharide (HA6) and octasaccharide (HA8), 0.8 mL high-molecular-weight HA (2 g/L), 8 μl HAase ($2.43 \times 10^5$ U/mL) and appropriate amount of citrate buffer (pH5.5) are mixed to form 1 mL reaction system. The mixture is incubated at 38° C. for 6 hours to generate HA4, HA6 and HA8.

To produce tetrasaccharide (HA4), hexasaccharide (HA6), octasaccharide (HA8) and decasaccharide (HA10), 0.8 mL high-molecular-weight HA (2 g/L), 10 μl HAase ($2.43 \times 10^5$ U/mL) and appropriate amount of citrate buffer (pH5.5) are mixed to form 1 mL reaction system. The mixture is incubated at 38° C. for 5 hours to generate HA4, HA6, HA8 and HA10.

This invention provides a novel leech HAase gene and a method of high-level heterologous expression of the leech HAase. By controlling the incubation condition, different HA oligosaccharides, particularly HA4, HA6, HA8 and HA10, can be selectively generated using the leech HAase. The large-scale expression of leech HAase and the enzymatic production of specific HA oligosaccharides are not only useful in the cosmetic, healthcare and the medical industries but also have applications in polysaccharides chemical synthesis and cancer research.

EXAMPLES

Materials and Methods

YPD medium: 10 g·L$^{-1}$ yeast extract, 20 g·L$^{-1}$ peptone, 20 g·L$^{-1}$ dextrose.

BMGY (Buffered minimal glycerol yeast medium) medium: 20 g·L$^{-1}$ peptone, 10 g·L$^{-1}$ yeast extract, 3 g·L$^{-1}$ K 11.8 g·L$^{-1}$ KH$_2$PO$_4$, 13.4 g L$^{-1}$ YNB, $4 \times 10^{-4}$ g L$^{-1}$ biotin, 10 mL L$^{-1}$ glycerol.

BMMY (Buffered methanol minimal yeast medium) medium: 20 g·L$^{-1}$ peptone, 10 g·L$^{-1}$ yeast extract, 3 g·L$^{-1}$ K$_2$HPO$_4$, 11.8 g·L$^{-1}$ KH$_2$PO$_4$, 13.4 g L$^{-1}$ YNB, $4 \times 10^{-4}$ g L$^{-1}$ biotin, 5 mL L$^{-1}$ methanol.

HAase activity is quantified by measuring the amount of reducing sugar liberated from HA, which is determined by a 3,5-dinitrosalicylic acid (DNS) colorimetric spectrophotometric method. One unit of HAase activity is defined as the amount of enzyme that needs to release reducing sugar equivalent to 1 μg glucose per hour from HA at 38° C. and pH 5.5.

The presence of HAase activity is determined using the simple plate assay. The assay plate is prepared with 1 mg/mL HA, 1.5% agarose, 50 mM sodium citrate buffer (pH 5.3), 150 mM NaCl and 0.02% Na3N. The fermentation broth is poured into cylindrical holes on the agarose plates covered with 10% (w/v) cetylpyridinium chloride, and incubated at 37° C. for 10 hours. The formation of a distinct clear halo around the hole indicates the presence of HAase activity.

Leech HAase activity is quantified by measuring the amount of reducing sugar liberated from HA, which is determined by the 3,5-dinitrosalicylic acid (DNS) colorimetric spectrophotometric method. 2 mg/mL HA solution is prepared by dissolving HA in 50 mM citric acid-disodium hydrogen phosphate buffer (pH 5.5). 400 μL HA solution, 100 μL supernatant of the recombinant strain fermentation broth and buffer (50 mM citric acid-disodium hydrogen phosphate buffer, pH 5.5) are mixed to get 1 mL reaction system. The fermentation broth supernatant of the strains without HAase gene is used as a negative control. The mixture is incubated at 38° C. for 20 min. The reaction is stopped by immersion in boiling water.

Example 1

Clone of the Leech HAase Gene

Total RNA was extracted from the heads of wild leeches using a tissue total RNA extraction kit (Hangzhou Biosci Co., Ltd, China.). cDNA was synthesised in a 20 μL reaction system (5× First-Strand buffer 4 μL, 50 μM Oligo (dT)18 Primer 1 μL, 10 mM dNTP, 1 μL, 40 μL RNase Inhibitor 1 μL, 200 U/μL M-MLV 1 μl RNA 12 μL) using the M-MIV First Strand RT kit (Hangzhou Biosci Co., Ltd, China.).

The 3' end of the leech HAase gene was amplified with gene-specific primers

```
(EST1:   CTGGTGMYCACRTAACYGCTTTTAC;  (SEQ ID NO: 4)
EST2:    TCAACATACCTTGAYGCYWCWTA,    (SEQ ID NO: 5))
``` which were designed based on candidate hyaluronidase mRNA (GenBank: JZ186329.1 and GenBank: FP652258.1) similar to heparanases from a *Herudo medicinalis* EST database. The one-letter code for nucleotide sequence characters used herein is in accordance with WIPO Standard ST 0.25. PCRs were performed using gene-specific primers as the sense primer, the Oligo (dT) 18 as the antisense primer and the leech cDNAs as template. According to the 3' end sequence of PCR products, reverse primers were designed and the 5' end of the leech HAase gene was obtained by SMART RACE cDNA Amplification Kit. A putative 1470 bp open reading frame (ORF) was identified based on the 3'- and 5'-ends sequence, and primers were designed to amplify the full-length HAase cDNA. The PCR products were sequenced and the nucleotide sequence of leech HAase was confirmed (HaseA3887, SEQ ID NO.1).

Example 2

Construction of Recombinant Strains

To construct pPIC9K-HaseA3887, the leech HAase gene, HaseA3887 was amplified with primers A3887BYF/A3887BYR.

```
A3887BYF:
                                    (SEQ ID NO: 6)
CCGGAATTCATGAAAGAGATCGCGGTGACAATTGAC

A3887BYR:
                                    (SEQ ID NO: 7)
TCCGCGGCCGCTTATTTTTTGCACGCTTCAACGTTAGC
```

EcoRI/Not I restriction sites were introduced to the 5' and 3' ends of HaseA3887 respectively. The purified PCR products were digested with EcoRI/Not I and ligated to EcoRI/NotI-digested pPIC9K to obtain the pPIC9K-HaseA3887 plasmid.

To construct pPIC9K-His-HaseA3887, of which 6 His tags were fused to the N-terminus of HaseA3887, the HaseA3887 was amplified with primers BYA3887HF/BYA3887R.

```
BYA3887HF (SEQ ID NO: 8):
CCGGAATTCCACCACCACCACCACCACATGAAAGAGATCGCGGTGACAAT
AGAC

BYA3887R (SEQ ID NO: 9):
TCCGCGGCCGCTTATTTTTTGCACGCTTCAACGTTAGC
```

EcoRI/Not I restriction sites were introduced to the 5' and 3' ends of His-HaseA3887 (SEQ ID NO:2) respectively. The purified PCR products were digested with EcoRI/Not I and ligated to EcoRI/NotI-digested pPIC9K to obtain the pPIC9K-His-HaseA3887 plasmid.

The recombinant plasmids were transformed into chemically competent E. *Coli* DH5 prepared using standard CaCl2 methods. The identified recombinant plasmids were linearized with Sal I and transformed into *Pichia pastoris* GS115 by electroporation. The recombinant strain *P. pastoris* GS115/pPIC9K which contained the empty plasmid pPIC9K was set as a negative control.

Example 3

Overexpression of HaseA3887

Positive *P. pastoris* GS115 recombinants were cultivated in YPD medium at 30° C., 200 rpm for 16 hours. 10 mL seed culture was transferred into 100 mL BMGY medium and cultivated in 500-mL Erlenmeyer flasks rocking at 200 rpm, 30° C. When OD600 of the yeast culture reached 4, the cells were collected and transferred into 100 mL BMMY medium and cultivated in 500-mL Erlenmeyer flasks rocking at 200 rpm, 30° C. for 96 hours. The culture was added 0.5%-1.0% methanol every 24 hours.

Figure 1:
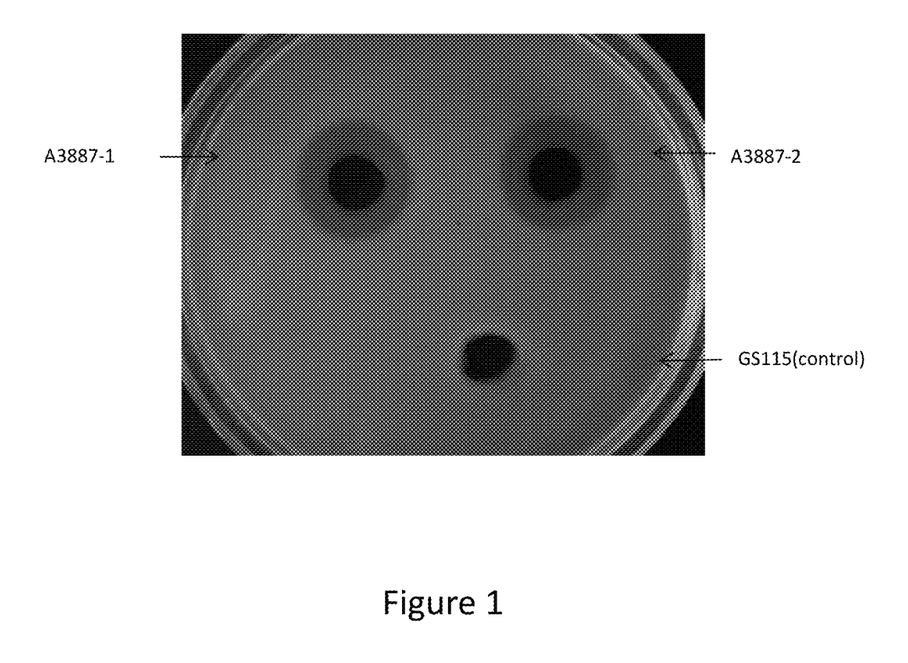
FIG. 1. Determination of HAase activity using a typical plate assay. A3887-1 and A3887-2 were two samples of *P. pastoris* GS115/pPIC9K-HaseA3887 fermentation broth; *P. pastoris* GS115 is the negative control.
Figure 2:
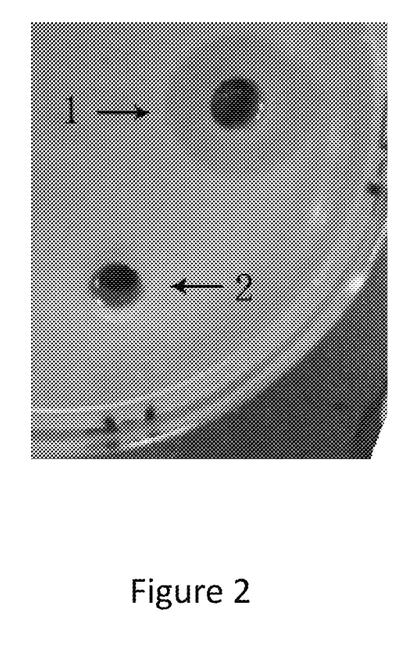
FIG. 2. Determination of HAase activity using a typical plate assay. 1, A3887HF, supernatant of *P. pastoris* GS115/pPIC9K-His-HaseA3887 fermentation broth; 2, supernatant of pPIC9k-GS115 fermentation broth (negative control).

As shown in FIG. 1 and FIG. 2, HA hydrolysis by the culture supernatant of both *P. pastoris* GS115/pPIC9K-HaseA3887 and *P. pastoris* GS115/pPIC9K-His-HaseA3887 produced clear transparent zones, indicating the presence of HAase activity. It demonstrated that the HaseA3887 does encode a HAase and it can be functionally overexpressed in *P. pastoris* GS115.

Figure 3:
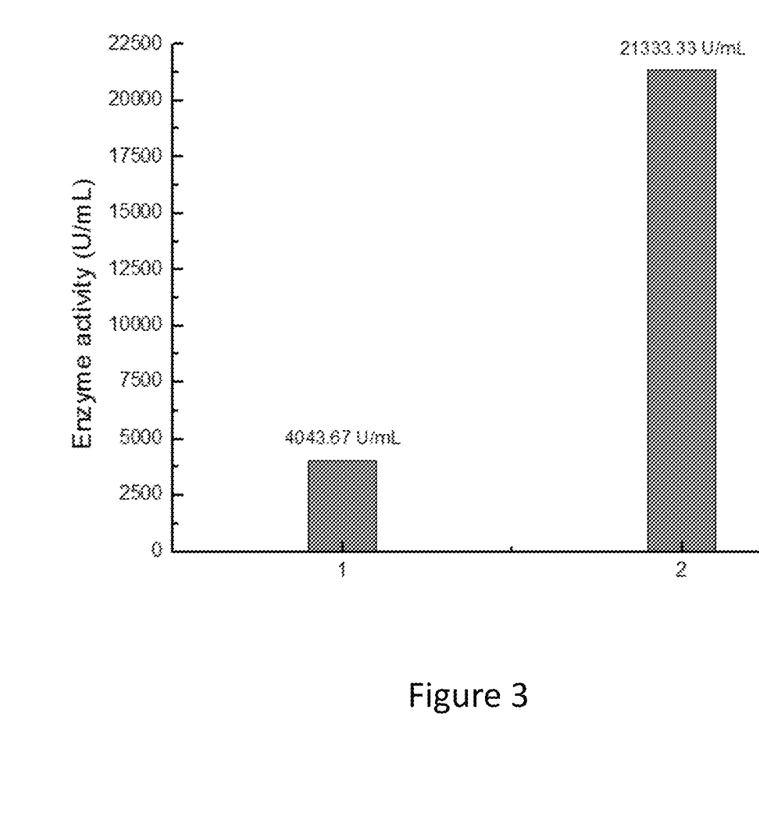
FIG. 3. HAase activity of shake flask fermentation broth determined by DNS method. 1, HAase activity of recombinant strain *P. pastoris* GS115/pPIC9K-HaseA3887; 2, HAase activity of recombinant strain *P. pastoris* GS115/pPIC9K-His-HaseA3887.

As shown in FIG. 3, flask cultivation demonstrated that HAase was successfully expressed and secreted into culture medium with final HAase activity of 21333.33 U/mL for *P. pastoris* GS115/pPIC9K-His-HaseA3887 and 4043.67 U/mL for *P. pastoris* GS115/pPIC9K-HaseA3887, respectively.

Figure 4:
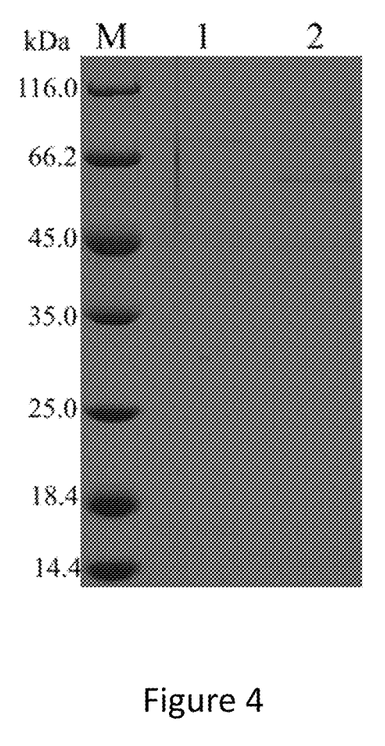
FIG. 4. SDS-PAGE analysis of recombinant leech HAase. M, molecular weight marker; 1, supernatant of *P. pastoris* GS115/pPIC9K fermentation broth; 2, supernatant of *P. pastoris* GS115/pPIC9K-HaseA3887 fermentation broth.
Figure 5:
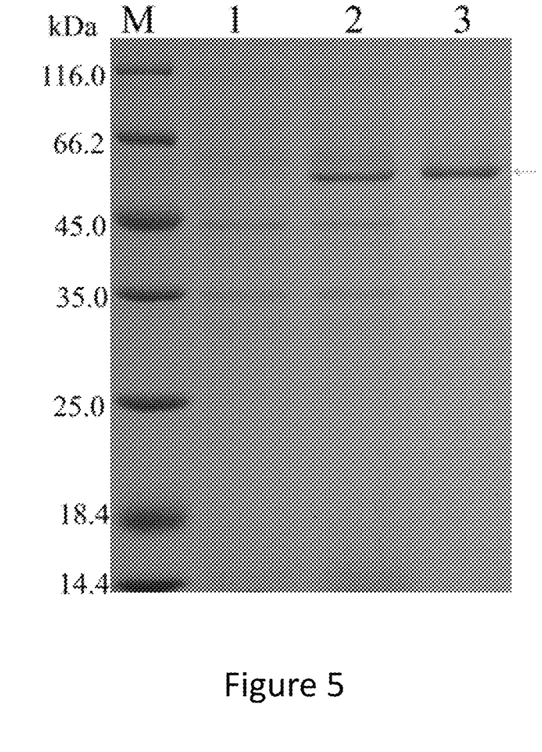
FIG. 5. SDS-PAGE analysis of recombinant leech HAase; M, molecular weight marker; 1, supernatant of *P. pastoris* GS115/pPIC9K fermentation broth; 2, supernatant of *P. pastoris* GS115/pPIC9K-His-HaseA3887 fermentation broth; 3, the purified enzyme.

The supernatant of fermentation broth and the purified enzyme were analysed by SDS-PAGE. As shown in FIG. 4 and FIG. 5, a protein band with an apparent molecular weight of 58 kDa was observed in *P. pastoris* GS115/pPIC9K-HaseA3887 and *P. pastoris* GS115/pPIC9K-His-HaseA3887 culture medium, but not in *P. pastoris* GS115/pPIC9K culture medium. It also supported the fact that the HAase had been successfully expressed and secreted into medium.

In addition, it was unexpected to find that fusing 6×His tag to the N-terminus of HaseA3887 not only made the purification process easier but also significantly increased secreted HAase activity from 4043.67 U/mL to 21333.33 U/mL.

Example 4

Purification of HaseA3887

The fermentation supernatant which had been filtered through a 0.45 μm filter membrane was loaded onto a gravity-flow column filled with Ni-NTA agarose and incubated at 4° C. for 2 hours. The impurities were washed with a stepwise gradient of imidazole (0, 10, 20, 30, 40, 50 mM) in a phosphate buffer. The bound N-terminal His-tagged protein was then eluted from the column with a phosphate buffer containing 500 mM imidazole, and finally dialyzed with a stepwise gradient of NaCl solution (300, 100, 0 mM) to remove salts and imidazole, and obtain the pure protein (FIG. 5).

Example 5

Production of HA8 and HA10 by the Leech HAase

The high-molecular-weight HA was prepared at a concentration of 2 g/L in 50 mM citrate buffer (pH 5.5). The HAase made by the method of Example 4 was diluted in water to make a solution with a concentration of 2.43×10⁵ U/mL.

Figure 6:
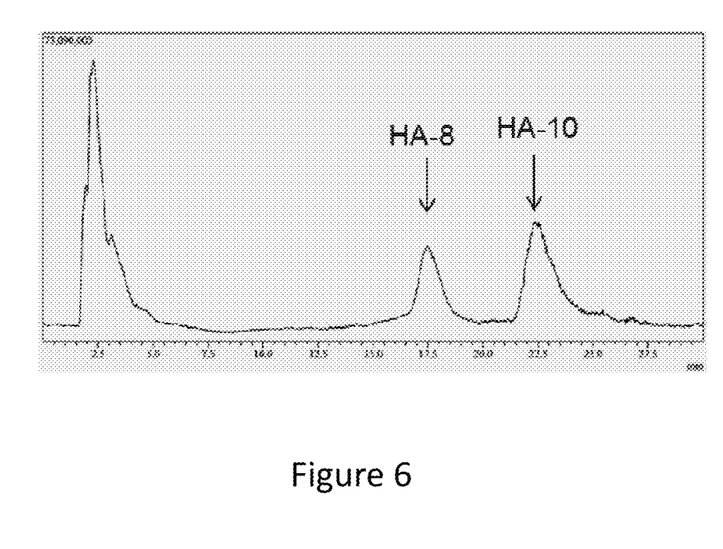
FIG. 6. LC-MS-IT-TOF profile of leech HAase-catalyzed HA hydrolysis.

To produce HA10 and HA8, 0.8 mL HA (2 g/L), 8 µl HAase (2.43×10⁵ U/mL) and appropriate amount of citrate buffer (pH5.5) were mixed to form 1 mL reaction system. The mixture was incubated at 38° C. for 4 hours to generate HA10 and HA8. The mixture was heated in boiling water to terminate the reaction. Then, the mixture was filtered through a 0.22 µm filter and analyzed with LCMS-IT-TOF (liquid chromatograph ion trap and time-of-flight mass spectrometry). Two prominent ion peaks corresponding to HA10 (955.78 [M-2H]$^{2-}$) and HA8 (766.22[M-2H]$^{2-}$) were shown in the LCMS-IT-TOF analysis chart (FIG. 6).

Example 6

Production of HA4 and HA6 by the Leech HAase

The high-molecular-weight HA was prepared at a concentration of 2 g/L in 50 mM citrate buffer (pH 5.5). The HAase made by the method of Example 4 was diluted in water to make a solution with a concentration of 2.43×10⁵ U/mL.

Figure 7:
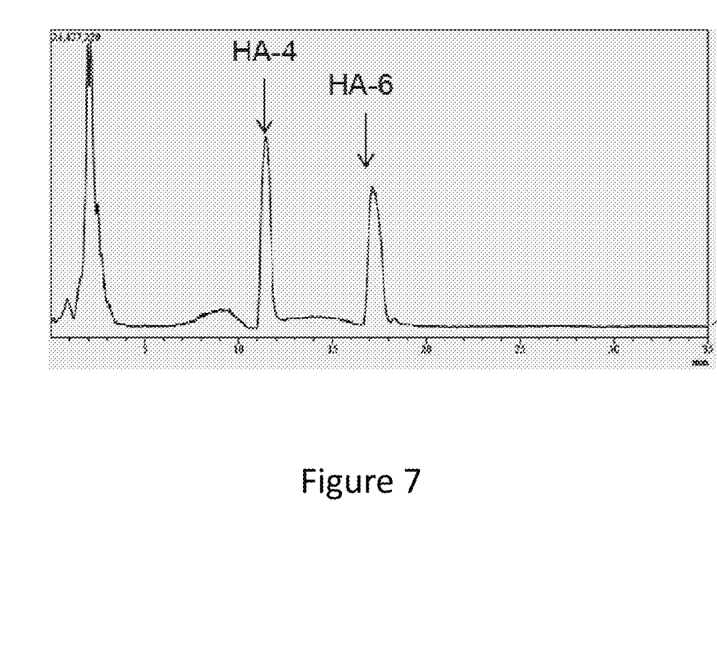
FIG. 7. LC-MS-IT-TOF profile of leech HAase-catalyzed HA hydrolysis.

To produce HA4 and HA6, 0.8 mL HA (2 g/L), 41 µl HAase (2.43×10⁵ U/mL) and appropriate amount of citrate buffer (pH5.5) were mixed to form 1 mL reaction system. The mixture was incubated at 38° C. for 8 hours to generate HA4 and HA6. The mixture was heated in boiling water to terminate the reaction. Then, the mixture was filtered through a 0.22 µm filter and analyzed with LCMS-IT-TOF. Two prominent ion peaks corresponding to HA4 (775.22[M-H]$^{-}$) and HA6 (576.66[M-2H]$^{2-}$) were shown in the LCMS-IT-TOF analysis chart (FIG. 7).

Example 7

Production of Low-Molecular-Weight HA Mixture by the Leech HAase

The high-molecular-weight HA was prepared at a concentration of 2 g/L in 50 mM citrate buffer (pH5.5). The HAase made by the method of Example 4 was diluted in water to make a solution with a concentration of 2.43×10⁵ U/mL.

Figure 8:
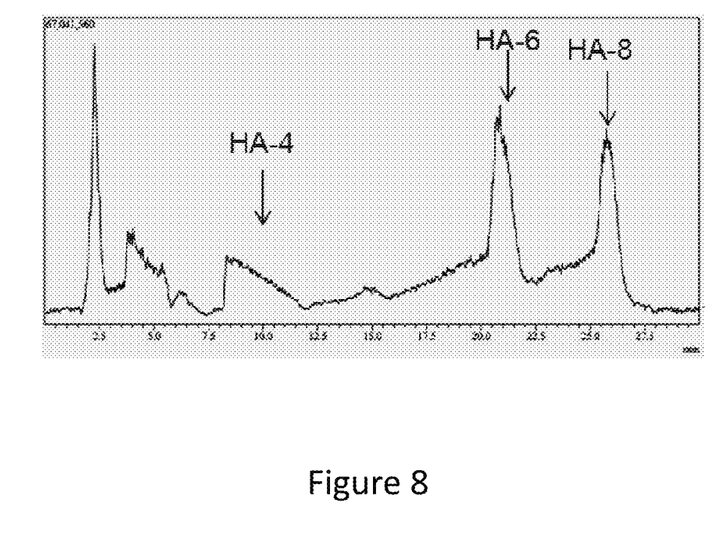
FIG. 8. LC-MS-IT-TOF profile of leech HAase-catalyzed HA hydrolysis.

To produce the mixture of HA4, HA6 and HA8, 0.8 mL HA (2 g/L), 8 µl HAase (2.43×10⁵ U/mL) and appropriate amount of citrate buffer (pH5.5) were mixed to form 1 mL reaction system. The mixture was incubated at 38° C. for 6 hours to generate HA4, HA6 and HA8. Then, the mixture was filtered through a 0.22 µm filter and analyzed with LCMS-IT-TOF. Three prominent ion peaks corresponding to HA4 (775.22 [M-H]$^{-}$), HA6 (576.66[M-2H]$^{2-}$) and HA8 (766.22[M-2H]$^{2-}$) were shown in the LCMS-IT-TOF analysis chart (FIG. 8).

Figure 9:
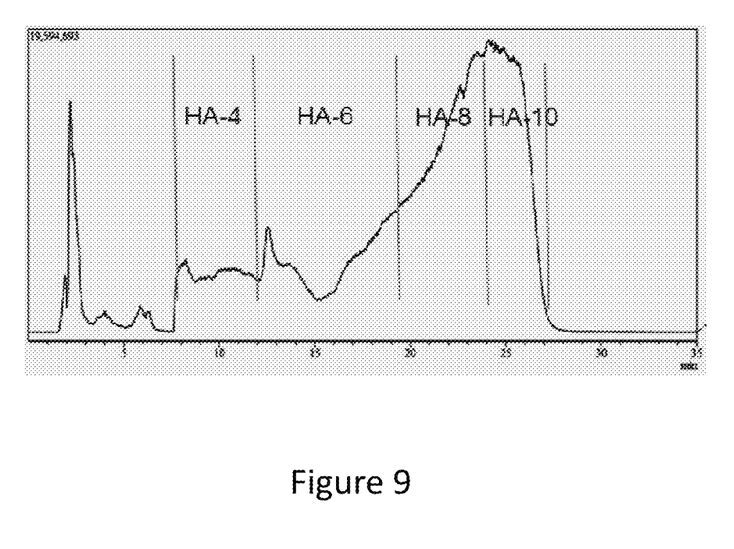
FIG. 9. LC-MS-IT-TOF profile of leech HAase-catalyzed HA hydrolysis.

To produce tetrasaccharide (HA4), hexasaccharide (HA6), octasaccharide (HA8) and decasaccharide (HA10), 0.8 mL HA (2 g/L), 10 µl HAase (2.43×10⁵ U/mL) and appropriate amount of citrate buffer (pH5.5) were mixed to form 1 mL reaction system. The mixture was incubated at 38° C. for 5 hours to generate HA4, HA6, HA8 and HA10. Four prominent ion peaks corresponding to HA4 (775.22[M-H]$^{-}$), HA6 (576.66[M-2H]$^{2-}$), HA8 (766.22[M-2H]$^{2-}$) and HA10 (955.78[M-2H]$^{2-}$) were shown in the LCMS0IT-TOF analysis chart (FIG. 9).

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

```
Seq ID NO: 1
atgaaagaga tcgcggtgac aattgacgat aagaacgtta ttgcctctgt cagcgagtca      60
ttccatggtg ttgcctttga tgcgtcgtta ttttcaccga aggggttgtg gagctttgtt     120
gacattacct caccgaaatt gtttaaactc ttggagggtc tctctcctgg ttacttcagg     180
gttggaggaa cgtttgctaa ctggctgttc tttgacttag atgaaaataa taagtggaaa     240
gactattggg cttttaaaga taaaacaccc gagactgcaa caatcacaag gaggtggctg     300
tttcgaaaac aaaacaacct gaaaaaagag acttttgacg acttagtcaa actaaccaaa     360
ggaagcaaaa tgagactgtt atttgattta aacgctgaag tgagaactgg ttatgaaatt     420
ggaaagaaaa tgacatccac ttgggatagc tcggaagctg aaaaattatt caaatactgt     480
gtgtcaaaag gttatggaga taatattgat tgggaacttg gtaatgaacc ggaccatacc     540
tccgcacaca atcttactga aaagcaagtt ggagaggact ttaaagcccT gcataaagtg     600
ctagagaaat atccgacgtt gaataaagga tcgcttgttg gacctgacgt tggatggatg     660
ggagtctctt atgtgaaagg attagcagac ggggctggtg atcacgtaac cgctttact     720 cttcatcagt attattttga cggcaatacc tcagatgtgt caacatacct tgacgctact     780
tattttaaaa aacttcaaca gctgtttgac aaagttaagg atgtcttgaa aaattctcca     840
cataaagata aaccgctctg gcttggagaa acaagttctg gatacaacag cggcacaaaa     900
gatgtatccg atcgatatgt tagcggattt ctaacattgg acaagttggg actcagtgca     960
gcgaacaatg tgaaagttgt gataagacaa acgatctata atggatacta cggacttctt    1020
gataaaaata ctctagagcc aaatccggat tattggctaa tgcatgttca caattctctg    1080
gttggaaata cggttttttaa agttgacgtt agtgacccta caaataaagc tagagtttat    1140
```

-continued

```
gcacagtgca ccaaaacaaa tagcaaacat actcagagta gatactacaa gggctcattg    1200
acgatctttg ctcttaatgt tggagatgaa gatgtgacgt tgaagattga tcaatacagt    1260
ggaaaaaaga tttattcata tattctgacc ccagaaggcg gccaacttac atcacaaaaa    1320
gttcttttga atggaaaaga attaaaatta gtgtcggatc aattgccaga actgaatgca    1380
gacgagtcga aacctctttt cactctgtct ccaaagacat ttggattttt tgttgttagc    1440
gatgctaacg ttgaagcctg caaaaaataa                                    1470
```

SEQ ID NO: 2
```
caccaccacc accaccacat gaaagagatc gcggtgacaa ttgacgataa gaacgttatt      60
gcctctgtca gcgagtcatt ccatggtgtt gcctttgatg cgtcgttatt ttcaccgaag    120
gggttgtgga gctttgttga cattacctca ccgaaattgt ttaaactctt ggagggtctc    180
tctcctggtt acttcagggt tggaggaacg tttgctaact ggctgttctt tgacttagat    240
gaaaataata agtggaaaga ctattgggct tttaaagata aacacccga gactgcaaca    300 atcacaagga ggtggctgtt tcgaaaacaa aacaacctga aaaagagac ttttgacgac    360 ttagtcaaac taaccaaagg aagcaaaatg agactgttat tgatttaaa cgctgaagtg    420 agaactggtt atgaaattgg aaagaaatg acatccactt gggatagctc ggaagctgaa    480
aaattattca atactgtgt gtcaaaaggt tatggagata atattgattg ggaacttggt    540
aatgaaccgg accataccct cgcacacaat cttactgaaa agcaagttgg agaggacttt    600
aaagccctgc ataaagtgct agagaaatat ccgacgttga ataaaggatc gcttgttgga    660
cctgacgttg gatggatggg agtctcttat gtgaaaggat tagcagacgg ggctggtgat    720
cacgtaaccg cttttactct tcatcagtat tattttgacg gcaataccct agatgtgtca    780
acataccttg acgctactta ttttaaaaaa cttcaacagc tgtttgacaa agttaaggat    840
gtcttgaaaa attctccaca taaagataaa ccgctctggc ttggagaaac aagttctgga    900
tacaacagcg gcacaaaaga tgtatccgat cgatatgtta gcggatttct aacattggac    960
aagttgggac tcagtgcagc gaacaatgtg aaagttgtga taagacaaac gatctataat   1020
ggatactacg gacttcttga taaaaatact ctagagccaa atccggatta ttggctaatg   1080
catgttcaca attctctggt tggaaatacg gttttttaaag ttgacgttag tgaccctaca   1140
aataaagcta gagtttatgc acagtgcacc aaaacaaata gcaaacatac tcagagtaga   1200
tactacaagg gctcattgac gatctttgct cttaatgttg gagatgaaga tgtgacgttg   1260
aagattgatc aatacagtgg aaaaaagatt tattcatata ttctgacccc agaaggcggc   1320
caacttacat cacaaaaagt tcttttgaat ggaaaagaat aaaattagt gtcggatcaa   1380 ttgccagaac tgaatgcaga cgagtcgaaa acctctttca ctctgtctcc aaagacattt   1440
ggattttttg ttgttagcga tgctaacgtt gaagcctgca aaaaataa              1488
```

SEQ ID NO: 3
```
Met Lys Glu Ile Ala Val Thr Ile Asp Asp Lys Asn Val Ile Ala Ser
1               5                   10                  15

Val Ser Glu Ser Phe His Gly Val Ala Phe Asp Ala Ser Leu Phe Ser
            20                  25                  30

Pro Lys Gly Leu Trp Ser Phe Val Asp Ile Thr Ser Pro Lys Leu Phe
        35                  40                  45

Lys Leu Leu Glu Gly Leu Ser Pro Gly Tyr Phe Arg Val Gly Gly Thr
    50                  55                  60

Phe Ala Asn Trp Leu Phe Phe Asp Leu Asp Glu Asn Asn Lys Trp Lys
65                  70                  75                  80

Asp Tyr Trp Ala Phe Lys Asp Lys Thr Pro Glu Thr Ala Thr Ile Thr
```

-continued

```
                85                  90                  95
Arg Arg Trp Leu Phe Arg Lys Gln Asn Asn Leu Lys Lys Glu Thr Phe
            100                 105                 110

Asp Asp Leu Val Lys Leu Thr Lys Gly Ser Lys Met Arg Leu Leu Phe
        115                 120                 125

Asp Leu Asn Ala Glu Val Arg Thr Gly Tyr Glu Ile Gly Lys Lys Met
    130                 135                 140

Thr Ser Thr Trp Asp Ser Ser Glu Ala Glu Lys Leu Phe Lys Tyr Cys
145                 150                 155                 160

Val Ser Lys Gly Tyr Gly Asp Asn Ile Asp Trp Glu Leu Gly Asn Glu
                165                 170                 175

Pro Asp His Thr Ser Ala His Asn Leu Thr Glu Lys Gln Val Gly Glu
            180                 185                 190

Asp Phe Lys Ala Leu His Lys Val Leu Glu Lys Tyr Pro Thr Leu Asn
        195                 200                 205

Lys Gly Ser Leu Val Gly Pro Asp Val Gly Trp Met Gly Val Ser Tyr
    210                 215                 220

Val Lys Gly Leu Ala Asp Gly Ala Gly Asp His Val Thr Ala Phe Thr
225                 230                 235                 240

Leu His Gln Tyr Tyr Phe Asp Gly Asn Thr Ser Asp Val Ser Thr Tyr
                245                 250                 255

Leu Asp Ala Thr Tyr Phe Lys Lys Leu Gln Gln Leu Phe Asp Lys Val
            260                 265                 270

Lys Asp Val Leu Lys Asn Ser Pro His Lys Asp Lys Pro Leu Trp Leu
        275                 280                 285

Gly Glu Thr Ser Ser Gly Tyr Asn Ser Gly Thr Lys Asp Val Ser Asp
    290                 295                 300

Arg Tyr Val Ser Gly Phe Leu Thr Leu Asp Lys Leu Gly Leu Ser Ala
305                 310                 315                 320

Ala Asn Asn Val Lys Val Val Ile Arg Gln Thr Ile Tyr Asn Gly Tyr
                325                 330                 335

Tyr Gly Leu Leu Asp Lys Asn Thr Leu Glu Pro Asn Pro Asp Tyr Trp
            340                 345                 350

Leu Met His Val His Asn Ser Leu Val Gly Asn Thr Val Phe Lys Val
        355                 360                 365

Asp Val Ser Asp Pro Thr Asn Lys Ala Arg Val Tyr Ala Gln Cys Thr
    370                 375                 380

Lys Thr Asn Ser Lys His Thr Gln Ser Arg Tyr Tyr Lys Gly Ser Leu
385                 390                 395                 400

Thr Ile Phe Ala Leu Asn Val Gly Asp Glu Asp Val Thr Leu Lys Ile
                405                 410                 415

Asp Gln Tyr Ser Gly Lys Lys Ile Tyr Ser Tyr Ile Leu Thr Pro Glu
            420                 425                 430

Gly Gly Gln Leu Thr Ser Gln Lys Val Leu Leu Asn Gly Lys Glu Leu
        435                 440                 445

Lys Leu Val Ser Asp Gln Leu Pro Glu Leu Asn Ala Asp Glu Ser Lys
    450                 455                 460

Thr Ser Phe Thr Leu Ser Pro Lys Thr Phe Gly Phe Phe Val Val Ser
465                 470                 475                 480

Asp Ala Asn Val Glu Ala Cys Lys Lys
            485
```

What is claimed is:

1. An isolated cDNA sequence of a leech hyaluronidase (HAase), wherein the nucleotide sequence of said cDNA sequence encoding said leech HAase comprises a sequence set forth in SEQ ID NO:1.

2. A leech hyaluronidase with His tags, wherein said leech hyaluronidase with His tags is encoded by a nucleotide sequence set forth in SEQ ID NO: 2.

3. A cDNA sequence of a leech hyaluronidase with His tags, wherein the nucleotide sequence of said cDNA sequence is set forth in SEQ ID NO:2.

* * * * *

SEQUENCE LISTING

<160> NUMBER OF SEQ ID NOS: 9

<210> SEQ ID NO 1
<211> LENGTH: 1470
<212> TYPE: DNA
<213> ORGANISM: Leech

<400> SEQUENCE: 1

| | | | | | |
|---|---|---|---|---|---|
| atgaaagaga | tcgcggtgac | aattgacgat | aagaacgtta | ttgcctctgt | cagcgagtca | 60 |
| ttccatggtg | ttgcctttga | tgcgtcgtta | ttttcaccga | aggggttgtg | gagctttgtt | 120 |
| gacattacct | caccgaaatt | gtttaaactc | ttggagggtc | tctctcctgg | ttacttcagg | 180 |
| gttggaggaa | cgtttgctaa | ctggctgttc | tttgacttag | atgaaaataa | taagtggaaa | 240 |
| gactattggg | cttttaaaga | taaacacccc | gagactgcaa | caatcacaag | gaggtggctg | 300 |
| tttcgaaaac | aaaacaacct | gaaaaaagag | acttttgacg | acttagtcaa | actaaccaaa | 360 |
| ggaagcaaaa | tgagactgtt | atttgattta | aacgctgaag | tgagaactgg | ttatgaaatt | 420 |
| ggaaagaaaa | tgacatccac | ttgggatagc | tcggaagctg | aaaaattatt | caaatactgt | 480 |
| gtgtcaaaag | gttatggaga | taatattgat | tgggaacttg | gtaatgaacc | ggaccatacc | 540 |
| tccgcacaca | atcttactga | aaagcaagtt | ggagaggact | taaagcccct | gcataaagtg | 600 |
| ctagagaaat | atccgacgtt | gaataaagga | tcgcttgttg | gacctgacgt | tggatggatg | 660 |
| ggagtctctt | atgtgaaagg | attagcagac | ggggctggtg | atcacgtaac | cgcttttact | 720 |
| cttcatcagt | attattttga | cggcaatacc | tcagatgtgt | caacatacct | tgacgctact | 780 |
| tattttaaaa | aacttcaaca | gctgtttgac | aaagttaagg | atgtcttgaa | aaattctcca | 840 |
| cataaagata | aaccgctctg | gcttggagaa | caagttctg | datacaacag | cggcacaaaa | 900 |
| gatgtatccg | atcgatatgt | tagcggattt | ctaacattgg | acaagttggg | actcagtgca | 960 |
| gcgaacaatg | tgaaagttgt | gataagacaa | acgatctata | tggatacta | cggacttctt | 1020 |
| gataaaaata | ctctagagcc | aaatccggat | tattggctaa | tgcatgttca | caattctctg | 1080 |
| gttggaaata | cggtttttaa | agttgacgtt | agtgaccta | caaataaagc | tagagtttat | 1140 |
| gcacagtgca | ccaaaacaaa | tagcaaacat | actcagagta | gatactacaa | gggctcattg | 1200 |
| acgatctttg | ctcttaatgt | tggagatgaa | gatgtgacgt | tgaagattga | tcaatacagt | 1260 |
| ggaaaaaaga | tttattcata | tattctgacc | ccagaaggcg | gccaacttac | atcacaaaaa | 1320 |
| gttcttttga | atgaaaaaga | attaaaatta | gtgtcggatc | aattgccaga | actgaatgca | 1380 |
| gacgagtcga | aaacctcttt | cactctgtct | ccaaagacat | ttggatttt | tgttgttagc | 1440 |
| gatgctaacg | ttgaagcctg | caaaaaataa | | | | 1470 |

<210> SEQ ID NO 2
<211> LENGTH: 1488
<212> TYPE: DNA
<213> ORGANISM: Leech

<400> SEQUENCE: 2

| | | | | | |
|---|---|---|---|---|---|
| caccaccacc | accaccacat | gaaagagatc | gcggtgacaa | ttgacgataa | gaacgttatt | 60 |
| gcctctgtca | gcgagtcatt | ccatggtgtt | gcctttgatg | cgtcgttatt | ttcaccgaag | 120 |
| gggttgtgga | gctttgttga | cattacctca | ccgaaattgt | ttaaactctt | ggaggtctc | 180 |
| tctcctggtt | acttcagggt | tggaggaacg | tttgctaact | ggctgttctt | tgacttagat | 240 |
| gaaaataata | agtggaaaga | ctattgggct | tttaaagata | aacacccga | gactgcaaca | 300 |
| atcacaagga | ggtggctgtt | tcgaaaacaa | aacaacctga | aaaagagac | ttttgacgac | 360 |

```
ttagtcaaac taaccaaagg aagcaaaatg agactgttat ttgatttaaa cgctgaagtg    420
agaactggtt atgaaattgg aaagaaaatg acatccactt gggatagctc ggaagctgaa    480
aaattattca atactgtgt gtcaaaaggt tatggagata atattgattg gaacttggt     540
aatgaaccgg accataccte cgcacacaat cttactgaaa agcaagttgg agaggacttt    600
aaagccctgc ataaagtgct agagaaatat ccgacgttga ataaaggatc gcttgttgga    660
cctgacgttg gatggatggg agtctcttat gtgaaaggat tagcagacgg ggctggtgat    720
cacgtaaccg cttttactct tcatcagtat tattttgacg gcaataccte agatgtgtca    780
acatacctt g acgctactta ttttaaaaaa cttcaacagc tgtttgacaa agttaaggat    840
gtcttgaaaa attctccaca taaagataaa ccgctctggc ttggagaaac aagttctgga    900
tacaacagcg gcacaaaaga tgtatccgat cgatatgtta gcggatttct aacattggac    960
aagttgggac tcagtgcagc gaacaatgtg aaagttgtga taagacaaac gatctataat   1020
ggatactacg gacttcttga taaaaatact ctagagccaa atccggatta ttggctaatg   1080
catgttcaca attctctggt tggaaatacg ttttttaaag ttgacgttag tgaccctaca   1140
aataaagcta gagtttatgc acagtgcacc aaaacaaata gcaaacatac tcagagtaga   1200
tactacaagg gctcattgac gatctttgct cttaatgttg gagatgaaga tgtgacgttg   1260
aagattgatc aatacagtgg aaaaaagatt tattcatata ttctgacccc agaaggcggc   1320
caacttacat cacaaaaagt tcttttgaat ggaaaagaat taaaattagt gtcggatcaa   1380
ttgccagaac tgaatgcaga cgagtcgaaa acctctttca ctctgtctcc aaagacattt   1440
ggatttttg ttgttagcga tgctaacgtt gaagcctgca aaaaataa                 1488
```

<210> SEQ ID NO 3
<211> LENGTH: 489
<212> TYPE: PRT
<213> ORGANISM: Leech

<400> SEQUENCE: 3

Met Lys Glu Ile Ala Val Thr Ile Asp Asp Lys Asn Val Ile Ala Ser
1               5                   10                  15

Val Ser Glu Ser Phe His Gly Val Ala Phe Asp Ala Ser Leu Phe Ser
            20                  25                  30

Pro Lys Gly Leu Trp Ser Phe Val Asp Ile Thr Ser Pro Lys Leu Phe
        35                  40                  45

Lys Leu Leu Glu Gly Leu Ser Pro Gly Tyr Phe Arg Val Gly Gly Thr
    50                  55                  60

Phe Ala Asn Trp Leu Phe Phe Asp Leu Asp Glu Asn Asn Lys Trp Lys
65                  70                  75                  80

Asp Tyr Trp Ala Phe Lys Asp Lys Thr Pro Glu Thr Ala Thr Ile Thr
                85                  90                  95

Arg Arg Trp Leu Phe Arg Lys Gln Asn Asn Leu Lys Lys Glu Thr Phe
            100                 105                 110

Asp Asp Leu Val Lys Leu Thr Lys Gly Ser Lys Met Arg Leu Leu Phe
        115                 120                 125

Asp Leu Asn Ala Glu Val Arg Thr Gly Tyr Glu Ile Gly Lys Lys Met
    130                 135                 140

Thr Ser Thr Trp Asp Ser Ser Glu Ala Glu Lys Leu Phe Lys Tyr Cys
145                 150                 155                 160

Val Ser Lys Gly Tyr Gly Asp Asn Ile Asp Trp Glu Leu Gly Asn Glu
                165                 170                 175

-continued

```
Pro Asp His Thr Ser Ala His Asn Leu Thr Glu Lys Gln Val Gly Glu
            180                 185                 190

Asp Phe Lys Ala Leu His Lys Val Leu Glu Lys Tyr Pro Thr Leu Asn
        195                 200                 205

Lys Gly Ser Leu Val Gly Pro Asp Val Gly Trp Met Gly Val Ser Tyr
    210                 215                 220

Val Lys Gly Leu Ala Asp Gly Ala Gly Asp His Val Thr Ala Phe Thr
225                 230                 235                 240

Leu His Gln Tyr Tyr Phe Asp Gly Asn Thr Ser Asp Val Ser Thr Tyr
                245                 250                 255

Leu Asp Ala Thr Tyr Phe Lys Lys Leu Gln Gln Leu Phe Asp Lys Val
            260                 265                 270

Lys Asp Val Leu Lys Asn Ser Pro His Lys Asp Lys Pro Leu Trp Leu
        275                 280                 285

Gly Glu Thr Ser Ser Gly Tyr Asn Ser Gly Thr Lys Asp Val Ser Asp
    290                 295                 300

Arg Tyr Val Ser Gly Phe Leu Thr Leu Asp Lys Leu Gly Leu Ser Ala
305                 310                 315                 320

Ala Asn Asn Val Lys Val Val Ile Arg Gln Thr Ile Tyr Asn Gly Tyr
                325                 330                 335

Tyr Gly Leu Leu Asp Lys Asn Thr Leu Glu Pro Asn Pro Asp Tyr Trp
            340                 345                 350

Leu Met His Val His Asn Ser Leu Val Gly Asn Thr Val Phe Lys Val
        355                 360                 365

Asp Val Ser Asp Pro Thr Asn Lys Ala Arg Val Tyr Ala Gln Cys Thr
    370                 375                 380

Lys Thr Asn Ser Lys His Thr Gln Ser Arg Tyr Tyr Lys Gly Ser Leu
385                 390                 395                 400

Thr Ile Phe Ala Leu Asn Val Gly Asp Glu Asp Val Thr Leu Lys Ile
                405                 410                 415

Asp Gln Tyr Ser Gly Lys Lys Ile Tyr Ser Tyr Ile Leu Thr Pro Glu
            420                 425                 430

Gly Gly Gln Leu Thr Ser Gln Lys Val Leu Leu Asn Gly Lys Glu Leu
        435                 440                 445

Lys Leu Val Ser Asp Gln Leu Pro Glu Leu Asn Ala Asp Glu Ser Lys
    450                 455                 460

Thr Ser Phe Thr Leu Ser Pro Lys Thr Phe Gly Phe Phe Val Val Ser
465                 470                 475                 480

Asp Ala Asn Val Glu Ala Cys Lys Lys
                485

<210> SEQ ID NO 4
<211> LENGTH: 25
<212> TYPE: DNA
<213> ORGANISM: Unknown
<220> FEATURE:
<223> OTHER INFORMATION: DNA Primer

<400> SEQUENCE: 4
ctggtgmyca crtaacygct tttac                                         25

<210> SEQ ID NO 5
<211> LENGTH: 23
<212> TYPE: DNA
<213> ORGANISM: Unknown
<220> FEATURE:
```

-continued

```
<223> OTHER INFORMATION: DNA primer

<400> SEQUENCE: 5
tcaacatacc ttgaygcywc wta                                              23

<210> SEQ ID NO 6
<211> LENGTH: 36
<212> TYPE: DNA
<213> ORGANISM: Unknown
<220> FEATURE:
<223> OTHER INFORMATION: DNA primer

<400> SEQUENCE: 6
ccggaattca tgaaagagat cgcggtgaca attgac                                36

<210> SEQ ID NO 7
<211> LENGTH: 38
<212> TYPE: DNA
<213> ORGANISM: Unknown
<220> FEATURE:
<223> OTHER INFORMATION: DNA primer

<400> SEQUENCE: 7
tccgcggccg cttatttttt gcacgcttca acgttagc                              38

<210> SEQ ID NO 8
<211> LENGTH: 54
<212> TYPE: DNA
<213> ORGANISM: Unknown
<220> FEATURE:
<223> OTHER INFORMATION: DNA primer

<400> SEQUENCE: 8
ccggaattcc accaccacca ccaccacatg aaagagatcg cggtgacaat agac            54

<210> SEQ ID NO 9
<211> LENGTH: 38
<212> TYPE: DNA
<213> ORGANISM: Unknown
<220> FEATURE:
<223> OTHER INFORMATION: DNA primer

<400> SEQUENCE: 9
tccgcggccg cttatttttt gcacgcttca acgttagc                              38
```